United States Patent [19]

Horvath et al.

[11] Patent Number: 5,463,082

[45] Date of Patent: Oct. 31, 1995

[54] FLUOROUS MULTIPHASE SYSTEMS

[75] Inventors: Istvan T. Horvath, New Hope, Pa.; Jozsef Rabai, Clinton, N.J.

[73] Assignee: Exxon Research and Engireering Company, Florham Park, N.J.

[21] Appl. No.: 88,706

[22] Filed: Jul. 8, 1993

[51] Int. Cl.[6] .................. C07D 333/76; C07C 37/58; C07C 315/02; C07C 45/62
[52] U.S. Cl. .................. 549/46; 568/836; 568/34; 568/429; 585/252
[58] Field of Search .................. 549/46; 568/836, 568/34, 429

[56] References Cited

U.S. PATENT DOCUMENTS

| | | | |
|---|---|---|---|
| 4,124,456 | 11/1978 | Yagupolsky et al. | 204/59 R |
| 4,315,093 | 2/1982 | Keller et al. | 528/362 |
| 4,598,059 | 7/1986 | Goudriaan et al. | 502/228 |
| 4,793,931 | 9/1987 | Stevens et al. | 210/636 |
| 4,954,444 | 12/1987 | Eveleigh et al. | 435/181 |
| 5,079,155 | 9/1989 | Cox et al. | 435/181 |
| 5,158,880 | 10/1992 | Eveleigh | 435/180 |
| 5,245,064 | 9/1993 | Gassman et al. | 556/60 |
| 5,264,633 | 11/1993 | Hackenbruch et al. | 568/319 |
| 5,275,669 | 1/1994 | Van Der Puy et al. | 134/42 |

FOREIGN PATENT DOCUMENTS 0246103  11/1987  European Pat. Off. .

OTHER PUBLICATIONS

EP Search Report dated Oct. 11, 1994 for EP Application No. 94304877.7 (EP Equivalent to USSN 088,706).
Eveleigh, et al., Chemical Abstracts No. CA112(13):115074a (Spectra 2000, No. 140, Jun.–Jul. 1989) "Fluorocarbons and Affinity Chromatography Supports".
3M, UK Patent Specification No. 840,725, published Jul. 6, 1960 "Process of Perfluoralkylating Aromatic Compounds".
Dorset, "Binary Phase Behavior of Perfluoroalkanes", Macromolecules (1990), 23, 894–901.
Simandi (ed), *Dioxygen Activation and Homogeneous Catalytic Oxidation*, (1991) p. 171 Szeverenyi, "Cabalt Phtahalocyanine Catalysis . . . " Elsever, Amsterdam .
Kobos, "Fluorocarbon–Based Immobilization Method . . . " Anal. Chem. 60 (18) 1996 Sep. 15, 1988.

Umemoto, "Perfluoro–Polymer–Supported FITS Reagents" Tetrahedron letters, 25(1), 81–82 (1984).
Freed, "(£ Perfluoroheptyl–β, β–Dicyanovinyl) aminostyrenes . . . ." J. Fluorine Chem. 47 (1990) 219–225.
Lyons, "Azide activation of metlalophalo–cyanine complexes . . . " Applied Catalysis A:General 84 (1992) L1–L6.
Kobos, "A Novel Fluorocarbon–Based Immobilization Technology", Trends in Biotech. vol. 7 (Apr. 1989), p. 101.
Kuwahara, "Self Organization of Bilayer Assemblies in A fluorocarbon Medium", J.A.C.S. (1993), 115, 3002–3003.
Weber, "Oxygenation of Alkenes . . . " J. Molec. Cat., 78 (1993) L9–L13.
Kuntz, "Homogeneous Catalysis in Water", Chemtech (Sep. 1987), p. 570.
Uno, "Prep. of Perfluoroalkyl Azaarenes . . , " Tetrahedron, vol. 47 (32), pp. 6231–6242 (1991).
Scott, "The Solubility of Fluorocarbons," J.A.C.S. (Dec. 1948), vol. 70, pp. 4090–4093.

*Primary Examiner*—Richard L. Raymond
*Assistant Examiner*—Deborah Lambkin
*Attorney, Agent, or Firm*—Linda M. Scuorzo

[57] ABSTRACT

Stoichiometric and catalytic chemical transformations may be carried out in solution using novel fluorous multiphase systems (FMS). The term "fluorous" is defined as a carbon-fluorine bond rich organic molecule. The FMS consists of a fluorous phase containing a fluorous solvent, typically a fluorocarbon or a fluorohydrocarbon and a reagent or a catalyst containing a sufficient number of fluorous moieties to render it preferentially soluble in the fluorous solvent without impairing the ability of the catalyst or reagent to be effective in the reaction and while maintaining the reaction in a liquid or fluid phase. The nonfluorous solvent may be any suitable organic or nonorganic solvent(s) with limited or no solubility in the fluorous solvent that is effective for dissolving the reactant(s) and most desirably, for separating the resulting product(s). Typically, such solvents have a Hildebrand solubility parameter of at least about 18.0 MPa½. Appropriate fluorous moieties are linear, branched and carbocyclic fluorocarbon alkyl chains with high carbon numbers. FMS reagents and catalysts can be prepared by (1) fluorination (i.e., replacement of C—H bonds with fluorine); (2) fluorofunctionalization, e.g., the attachment of fluorous moieties to the reagents or catalysts; or (3) by total synthesis. The invention is useful in separations technology and in catalyst design and synthesis.

10 Claims, No Drawings

FLUOROUS MULTIPHASE SYSTEMS

FIELD OF THE INVENTION

This invention relates to novel compositions and processes for chemical transformation and reactive separation.

SUMMARY OF THE INVENTION

The present invention relates to stoichiometric and catalytic chemical transformations carried out in solution using fluorous multiphase systems (FMS). The term "fluorous" is defined as a carbon-fluorine bond rich organic molecule which is generated by replacing hydrogen atoms bonded to carbon atoms with fluorine. The FMS consists of a fluorous phase containing a first (i.e. fluorous) solvent, typically a fluorocarbon or a fluorohydrocarbon, either of the foregoing with or without substituent groups, and a reagent or a catalyst containing a sufficient number of fluorous moieties to render it preferentially soluble in the fluorous solvent (i.e. dissolved therein and located at the interface of the fluorous and nonfluorous phases). The nonfluorous i.e. the second solvent, may be any known organic or nonorganic solvent(s) with limited or no solubility in the fluorous solvent that is effective for dissolving the reactants and/or separating the reaction products. Typically a second solvent (i.e. nonfluorous solvent) having a Hildebrand solubility parameter of at least about 18.0 MPa½ is suitable. The reaction can occur simultaneously in the fluorous phase and at the interface of the phases. It is essential that the attached fluorous moieties do no impair the ability of the catalyst or reagent to be effective or participate in the reaction and while maintaining the reaction in a liquid or fluid phase. The most appropriate fluorous moieties are linear, branched and carbocyclic fluorocarbon alkyl chains with high carbon numbers that are effective to enable the catalyst or reagent to remain fluorous phase compatible. The fluorous moieties, optionally, may also contain O, S, N, P, As and Si, that assist in rendering the catalysts and reagents fluorous phase compatible. The FMS reagents and ligands can be prepared by: (1) fluorination (i.e., replacement of C—H bonds with fluorine); (2) fluorofunctionalization, e.g., the attachment of fluorous moieties to the reagents or catalysts; or (3) by total synthesis.

Many of the catalysts and reagents in the present invention are derivatives of known compounds. Thus they may be used in the reactions and for the purposes known in the art, with the added benefit that their reactive separation from nonfluorous compounds may be facilitated in a fluorous multiphase system.

The fluorous multiphase systems has utility for facilitating the separation of the FMS catalyst or spent FMS reagent. The possibility of separating the catalyst or the spent reagent from the products has utility in the design and synthesis of catalysts and reagents with high product selectivity, resulting in especially environmentally friendly processes, e.g., waste water elimination, metal waste removal.

DETAILED DESCRIPTION OF THE INVENTION

Embodiments of the present invention include the fluorous systems containing the FMS solvent with the dissolved FMS reagent or FMS catalyst forming the fluorous phase, and a second (nonfluorous) phase having some miscibility (to allow sufficient contact of reactants) with the fluorous phase. Also included are the products produced by the processes disclosed herein. Other embodiments of the present invention include the novel processes of preparing certain FMS reagents and FMS catalysts. Yet another embodiment of the invention is the method of using the fluorous moieties incorporated into the particular reagents and catalysts to enable them to function as described herein to effect chemical reactions and reactive separations.

The terms "liquid-containing multiphase system" and "multiphase system" means liquid-liquid biphase, or multiphase systems containing a liquid-liquid biphase. These systems are frequently used in various synthetic, catalytic and separation processes. The formation of a liquid-liquid multiphase system is the result of the limited or negligible solubility or miscibility of the liquids in each other at a given set of conditions (e.g., 25° C. and atmospheric pressure, 100 KPa, "ambient"). A commonly used combination is an aqueous biphase system which consists of water as one of the phases and mostly hydrocarbons as the other. Unfortunately, such systems cannot be used for water-sensitive chemical reactions, e.g., wherein one of the components of the system could undergo chemical reactions with water. Furthermore, large scale aqueous multiphase processes could generate large amounts of waste water. It would be advantageous if multiphase systems could be produced that obviate some of these difficulties.

The physical properties of partially or fully fluorinated hydrocarbons, especially perfluorinated alkanes, ethers, and tertiaryamines are unusual because of their nonpolar nature and low intermolecular forces. Water and alcohols are almost completely immiscible with fluorocarbons and the miscibility of most common organic solvents with fluorocarbons is low. Compounds having similar molecular volumes are typically immiscible if their Hildebrand solubility parameter difference at standard conditions is equal to or higher than about 4.0 MPa½, more typically, 5.7 MPa½. For additional parameter values, see CRC Handbook of Solubility Parameters and Other Cohesion Parameters, E. F. M. Barton, ed. (1983). For common perfluoroalkanes this would place the dividing line between complete miscibility and partial miscibility of the more common aliphatic fluorocarbons, such as $C_5$ (11.2 MPa½), $C_6$ (12.3 MPa½) and the like (e.g., $C_7$ to $C_9$, 12.3–12.7 MPa½) with other solvents, in the range of solvent solubility parameter values from about 17.4 to about 18.0 MPa½ (i.e., around that of para-xylene 18.0 MPa½). Above this point the miscibility declines with increasing solubility parameter values. Consequently, perfluoroalkanes, perfluoroalkylethers, perfluoroalkyltertiaryamines could be used to form biphase or multiphase systems at appropriate conditions. However, because the miscibility of liquids in multiphase systems is temperature and pressure dependent one phase systems are possible at appropriate conditions. However, it is desirable to generate more than one phase for purposes of separation.

As used herein the terms "fluorinated hydrocarbon" and "fluorohydrocarbon" include organic compounds in which at least one hydrogen atom bonded to a carbon atom is not replaced with a fluorine atom. The term "fluorocarbon" means one in which all hydrogen atoms bonded to carbon atoms are replaced with fluorine atoms. The term "fluorous" is defined as a carbon-fluorine bond rich organic molecule which is generated by replacing hydrogen atoms bonded to carbon atoms with fluorine (e.g., fluorocarbons, fluorohydrocarbons, and either of the foregoing with or without substituents). Typically this means that the "fluorous" organic molecule must contain a significant number of hydrogen atoms in C—H bonds replaced with fluorine atoms. Replacement with at least about 20 wt % fluorine to less than about 90 wt % of the total composition is desirable for FMS reagents and FMS catalysts. The fluorous solvent in which the FMS catalyst or reagent is dissolved (i.e. the first solvent) could be composed of any fluorocarbons or fluorohydrocarbons, either of the foregoing with or without functional groups provided there are minimal attractive interactions between those groups. Typically replacement of at least 50 wt % fluorine to total composition of the solvent molecules is desirable. The fluorous phase consists of the dissolved FMS catalyst or FMS reagent in the fluorous solvent. The fluorous solvent should have low or preferably no solubility in the other (i.e nonfluorous) phase in the case of systems that contain a liquid-liquid biphase. Herein the catalyst is referred to as "fluorous catalyst" or "FMS catalyst" and the reagent is referred to as a "fluorous reagent" or "FMS reagent". As used herein "reagent" means a compound that is used in a stoichiometric chemical transformation during which it becomes spent but wherein the spent reagent may be regenerated. The fluorous catalysts and reagents should be designed to contain effective amounts and types of fluorous moieties, $(R)_n(Rf)_m$, to render them fluorous phase compatible without affecting their activity and reactivity, respectively. Such fluorous moieties are suitably fluorohydrocarbon chains and/or fluorocarbon chains of appropriate length, number and structure to achieve the foregoing purposes.

The present invention teaches a significant advance in reaction processes and reactive separation technology. It allows tailoring of a known catalyst or reagent to render it preferentially fluorous phase-compatible while maintaining its ability to carry out or participate in reactions of the corresponding nonfluorous catalyst or reagent (i.e. the catalyst or reagent without the fluorous moiety). An advantage of the present invention is that it permits the carrying out of known reactions both catalytic and stoichiometric, the improvement being that incorporation of fluorous moieties in effective amounts to render the catalyst or reagent soluble in the fluorous phase allows the reactions to be carried out in a manner that facilitates separation of the fluorous catalyst or spent fluorous reagent from the reaction products, and essentially allows catalyst recycling and reagent regeneration. Additionally, according to the the present invention fluorous compatibilization of newly discovered catalysts and reagents also may be achieved and these will also have utility because they are soluble in fluorous solvents. Finally, fluorous systems have remarkable stability even in strongly oxidizing environments.

The process and compositions of the present invention have utility in that they enable known stoichiometric and catalytic reactions to be carried out in a fluorous phase environment thereby facilitating reactive separation of the fluorous catalyst or spent fluorous reagent from other compounds.

In general, an advantage of the present invention is the catalytic and stoichiometric reactions and separations related to the fluorous catalysts and reagents may be carried out within the range of reaction and system conditions and parameters e.g. temperature, pressure, and the like, typically used for the corresponding nonfluorous (parent) catalyst or reagent.

The present invention takes advantage of the limited miscibility or complete immiscibility of partially and fully fluorinated hydrocarbon compounds with nonfluorinated (organic and inorganic) compounds at appropriate conditions. The fluorous multiphase systems used in the present invention consist of: (1) a first solvent (i.e. "fluorous solvent") which is selected from the group consisting of fluorocarbons, fluorohydrocarbons, substituted fluorocarbons, and substituted fluorohydrocarbons and mixtures thereof containing a reagent (i.e. "fluorous reagent") or catalyst (i.e. "fluorous catalyst") which contains a sufficient number fluorous moieties having the formula, $(R)_n(Rf)_m$, wherein $(R)_n$ if present is a hydrocarbon domain, and wherein $(Rf)_m$ is at least one fluorous domain to render the reagent or catalyst preferentially soluble in or compatible with the solvent to form the fluorous phase; (2) at least one nonfluorous phase containing the reactants. For separation enhancement another solvent suitably any known organic or nonorganic compound having limited or no solubility in the fluorous phase may be used in which the reaction products are separable. It is acceptable that reaction product(s) alone constitute the product separation phase. Particularly when the solubilities of the reactants are very low in the fluorous phase the chemical reaction preferentially will occur at the interface.

The FMS reagent or FMS catalyst must be such that it dissolves preferentially or only in the fluorous solvent of the fluorous multiphase system. The FMS-compatible reagent or catalyst may be selected from the group consisting of fluorocarbon and fluorohydrocarbon rich molecules, either of the foregoing with or without functional groups. In the case of fluorocarbons the presence of structural features that create attractive interactions between the functional groups could limit the solubility in the fluorous solvent and should be minimized. Furthermore, the presence of structural features that allow attractive interactions with the constituents of the second (i.e. nonfluorous) phase could lead to leaching from the fluorous phase particularly where the second phase contains a liquid or fluid solvent. Such leaching is not generally desirable. In the case of fluorohydrocarbons most of the attractive interactions between the hydrocarbon domain, $(R)_n$, or the metal center of the molecule with the remainder of the molecule or with the constituents of the other phases should be limited by fluorous domains, $(Rf)_m$, of appropriate size, shape and number to avoid leaching. The most appropriate groups in this regard are linear, zigzagged (i.e. oxygen and sulfur-containing), carbocyclic, or branched. However, preferred are branched (i.e. branching through C or N frameworks) fluorocarbon chains. Higher carbon number chains are preferred (e.g., about $C_3$ to about $C_{25}$, more preferably about $C_3$ to about $C_{15}$), so long as solubility in the solvent can be maintained. The fluorocarbon chain may also include other functional groups, (e.g., aromatic rings), provided fluorous solvent solubility can be maintained.

Fluorous multiphase systems have particular, but not exclusive, applicability in reactions involving known reagents and known catalytic reactions. The peculiar physical properties of a fluorous phase may be used advantageously to provide unexpected solvent effects including altered reactivities and/or selectivities. In addition, the solubilities of nonfluorous organic compounds in a fluorous phase are much lower than in a hydrocarbon phase, so the application of fluorous multiphase system has utility to significantly alter product yields. The inherent structural features responsible for the solubility of the FMS reagent or catalyst in the fluorous phase may be used to alter both reactivities and selectivities. One of the most important advantages of fluorous multiphase systems is the potential ease of separation of the fluorous catalysts or the spent fluorous reagents from the reaction products.

FMS reagents and FMS catalysts may be obtained by a number of methods. Some reagents and ligands for catalysts may be purchased commercially. Examples of such reagents are: perfluorooctyl(p-fluorobenzene)iodonium trifluoromethanesulfonate, perfluorodecanoic acid, perfluoro-2,5-dimethyl-3,6-dioxanonanoic acid, perfluorooctane sulfonic acid (K salt), bis(heptafluoro-isopropyl)ketone. Examples of such ligands are: hexafluoroacetylacetone, heptafluorobutyronitrile 1H,1H,9H-hexadecafluoro-1-nonanol, decafluoro-2-methyl-3-oxahexanoic acid, 1H,1H-heptafluoro-1-butanol, 11H-eicosafluoroundecanoic acid, 1H,1H,11H-eicosafluoroundecanol-1, heptafluorobutyric acid. Others may be synthesized, by one or more of the following three methods: (1) fluorination of a starting reagent or catalyst, i.e. by full or partial replacement of hydrogen atoms bonded to carbon atoms of the parent catalyst or reagent with fluorine atoms to form the fluorous derivative; (2) fluorofunctionalization of a starting reagent or catalyst, i.e. by incorporation of fluorous moieties, $(Rf)_m$, which may contain, if necessary, appropriate hydrocarbon domain, $(R)_n$, therein; or (3) total synthesis, i.e de novo synthesis from appropriate building blocks.

When the structural requirements of the FMS catalyst or reagent allow the complete replacement of all hydrogens bonded to carbons, fluorination can be performed by either using $F_2$/inert gas mixture or other fluorinating agents, (e.g., $CoF_3$). Highly HF-soluble compounds can be perfluorinated by known electrochemical methods. Thermally stable aromatic C—H bond containing reagents and catalysts can be perfluoroalkylated using perfluoroalkyliodides at high temperatures, e.g. 200°–300° C. These reactions result in the replacement of hydrogen atoms in the aromatic C—H bonds with perfluoroalkyl chains. The addition of a perfluoroalkyl iodide to olefin functionalities on catalysts and reagents also can be used. In both cases thermal or photochemical activation can be applied. For the introduction of fluorous moieties (i.e. $(R)_n(Rf)_m$)) standard C—C coupling reactions could be used. In each instance, the result is a FMS reagent or FMS catalyst that is similar to the "parent" (nonfluorous) compound but contains at least one fluorous moiety of suitable length and structure to render the catalyst or reagent fluorous phase compatible.

In carrying out reactions using the FMS compatible catalysts or reagents, reaction conditions should be maintained such that the phases have sufficient fluidity to allow contact between the FMS reagent and other reactants or FMS catalyst and reactants, as the case may be, and to allow recovery or removal of the reaction products. The important aspect is to facilitate contact between the fluorous catalyst or fluorous reagent and the other reactants by appropriate methods e.g., agitation or other means of intimate contact. The result may be formation of a dispersion or emulsion. Preferably the FMS catalyst or FMS reagent should remain liquid or fluid during the reaction process, such that it remains dissolved in the fluorous solvent and at the interface at reaction conditions. The reaction may adversely be affected if sufficient contact can not be achieved. The processes disclosed herein are solution processes.

In order to effect reactive separation or extraction in the processes of the present invention it is desirable that the reaction products have low solubility in the fluorous solvent such that the fluorous catalyst or spent fluorous reagent and the reaction product(s) segregate or otherwise may be extracted into separate phases. Recovery of the reaction products may be accomplished by suitable methods that include multiphase formation if multiple phases were not present during reaction, e.g. by separation on standing, changing polarity of solvent, addition of co-solvents, temperature, pressure or other change of system conditions or parameters. Included in the term "multiphase system" are maintained as one liquid (fluid) phase (the fluorous phase) at system conditions but separate into multiphase systems, as well as biphase liquid and higher multiphase systems, upon changing those system conditions or parameters. Also included in the term systems are compositions that consist of a fluid (liquid) phase (the fluorous phase) and gas phase reactants.

The limited miscibility or immiscibility of the FMS catalyst or FMS reagent with nonfluorinated compounds and nonfluorinated (i.e. other) phases or solvents is an essential element for the separation processes disclosed herein. Ideally, fluorous phase compatibilization should be performed to such an extent that it provides high solubility of the FMS catalyst or reagent in the fluorous solvent and no solubility in the other phases. However, practically some degree of solubility is inevitable, but it should not be to a degree that substantially interferes with the reaction or, especially, with the separation process. Typically, miscibility of the fluorous solvent or solubility of the fluorous catalyst or reagent at the ppb level is acceptable. Solubility may be determined by adding the FMS catalyst or FMS reagent to the solvent or phase into which the product will be separated and determining the solubility level by known methods. Similarly, the partition of the FMS catalyst or FMS reagent can be determined by solvent pair experiments.

The other (nonfluorous) phase is suitably any one or more into which separation of the reaction products may be effected, and will depend on the characteristics of the particular reaction products. It should be noted that cases in which the reaction product is less polar than the reactants (e.g. hydrogenation of unsaturated hydrocarbons to fully saturated hydrocarbons), use of appropriate co-solvents and several extractions may be necessary.

Optionally, FMS phase transfer reagents such as (Rf)-COOH or $(Rf)SO_3H$ for aqueous-fluorous systems, and (perfluoro-octyl)benzene containing hydrocarbon and fluorocarbon domains for hydrocarbonfluorous systems may be added to facilitate entry of the reactants into the fluorous phase.

Chemical transformations can be effected in the fluorous multiphase system (i.e., in the fluorous phase and at the interface with the other phase) by FMS catalysts or reagents that contain at least one metal center or organic core. That is, catalysts and reagents known to those skilled in the art to effect or participate in known reactions are potential "parent" materials for making the fluorous phase compatible derivatives of the present invention. However, whether derived from a known parent compound or synthesized de novo, fluorous compatible catalysts and reagents of the present invention that contain at least one metal center, structurally may be represented according to the formula as below:

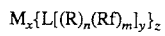

$$M_x\{L[(R)_n(Rf)_m]_y\}_z$$

In the above formula the FMS reagent or FMS catalyst contains at least one metal center to which at least one fluorous ligand having the formula, $L[(R)_n(Rf)_m]_y$ is bonded which ligand contains the fluorous moiety, i.e. $[(R)_n(Rf)_m]$, which includes the hydrocarbon domain, $(R)_n$, and the fluorous domain, $(Rf)_m$.

For organic-based FMS catalysts and reagents the formula is:

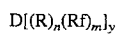

$$D[(R)_n(Rf)_m]_y$$

wherein D is an organic core to which at least one fluorous moiety is bonded, i.e. $[(R)_n(Rf)_m]$, which may include the hydrocarbon domain, $(R)_n$, and the fluorous domain, $(Rf)_m$.

In both the above formulas $(Rf)_m$ is a fluorous domain, $(R)_n$ is a hydrocarbon domain that may contain H and C, or may contain groups containing O, N, S, P, As and Si in addition to H and C in the backbone and/or as substituents, but wherein $(R)_n$ is hydrogen atom rich in comparison to $(Rf)_m$, and wherein n is an integer equal to at least zero or any whole number, preferably 0, 1, 2; and wherein m is any whole number; and wherein L is a ligand core containing C, N, O, P, As, S, Si and, in combination with the foregoing, H; and wherein y is the maximum number of fluorous moieties attachable to L or to D, as the case may be; and wherein z is the maximum number of ligands attachable to the metal M. Changing the ratio between n and m, could have major impact on the reactivity of a fluorous catalyst or reagent because fluorous domains are strongly electron withdrawing. Addition of hydrocarbon domains (at least about 2, preferably at least 3 "—$CH_2$—" groups, for example) as spacer groups between L or D and the fluorous domain generally reduces the electron withdrawing effect of the fluorous domain on M or D of the FMS catalyst or FMS reagent. The catalysts and reagents typically may contain a plurality of such fluorous moieties (i.e. y is greater than 1) having a significant proportion of fluorine atoms. By significant proportion is meant at least about about 20 wt %, preferably about 20 to 90 wt % more preferably from about 50 to 90 wt % of fluorine to total weight of the composition. Variability within $(R)_n$, $(Rf)_m$ and M or D may be introduced to accommodate catalysts or reagents having, for example, multiple metal centers, or variation in the types of ligands. Thus when the particular subscript n, m, y, or z is greater than 1 each n, m, y and z may be the same or different. In all such cases the foregoing should be present in number and structure that are effective to render the FMS catalyst or FMS reagent fluorous phase compatible. Incorporation of O, N, P, As, S, or Si into the carbon backbone of at least one fluorous domain, $(Rf)_m$, may assist in increasing the solubility in such situations. When hydrocarbon reactants are used in the fluorous environment they typically must have access to the metal center of the FMS catalyst or to the organic core of the FMS reagent in order to react. Inclusion of hydrocarbon domains, $(R)_n$, could facilitate hydrocarbon-hydrocarbon attractive interactions between the reactants and the hydrocarbon domains to enhance access to the reactive center.

The fluorous domain, $(Rf)_m$, typically will have a rodlike structure especially when derived from longer straight chain carbon containing backbones. It is essential that solubility or miscibility in the fluorous solvent be maintained to effect the catalytic or stoichiometric reaction. In addition to L, the FMS catalyst may contain other ligands. Typically, other ligands known in the art to be used in homogeneous catalysis for a particular reaction may be incorporated into the catalyst when the FMS catalyst is a modification or derivative of a known parent catalyst. Variability within $(R)_n$, $(Rf)_m$ and M or D may be introduced to accommodate systems having, for example, multiple metal centers, or variation in the types of ligands. Such systems are well known homogeneous catalysts or reagents and are amendable to fluorofunctionalization ("ponytailing") as described herein.

Thus, for example, for the novel catalyst Cl—Rh—{P[$CH_2$—$CH_2(CF_2)_6$F]$_3$}$_3$, (the nonfluorous parent compound of which is known as Wilkinson's catalyst, and is used for hydrogenation reactions) Rh corresponds to the $M_x$ wherein M=Rh, x=1;, P corresponds to L; $CH_2$—$CH_2$— corresponds to $(R)$, n=1; —$(CF_2)_6$—F to (Rf), m=1; the subscript 3 to y and the final subscript 3 to z. Similarly, for the FMS reagent, $CH_2$=P[$CH_2$—$CH_2(CF_2)_7CF_3$]$_3$, (the nonfluorous parent compound of which is known as the Wittig reagent), D in the above formula is $CH_2$=P; $CH_2CH_2$ is $(R)_n$, n=1; $(CF_2)_6$F is $(Rf)_m$ and m=1; 3 is y. Another FMS reagent of the same formula would be HOOC—[$CH_2$—$CH_2(CF_2)_7CF_3$]. Thus HOOC groups would correspond to D in the formula.

Perfluoroalkanes, perfluoroethers and perfluorotertiaryamines are suitable fluorous solvents. Typically such solvents are commercially available, or may be made by direct fluorination of known compounds.

By way of example of the utility of such processes are the following examples. Any number of other known processes, e.g. hydrogenation of unsaturated molecules, hydroformylation, polymerization of olefins, asymmetric hydrogenation, epoxidation, hydroformylation, carbon-carbon coupling, suitable may be practiced in accordance with the teaching of the present invention.

The development of a catalytic fluorous multiphase oxidation process for the conversion of light hydrocarbons could offer high yield synthesis of monooxygenates as the fluorous phase could have beneficial effects on side reactions. The very high solubility of $O_2$ in the fluorous phase could be an important factor of achieving economical reaction rates. For the catalytic oxidation reactions of the cyclohexene, the fluorous catalysts were prepared as in the examples by perfluoroalkylation of the parent complexes with perfluoroalkyliodides. This catalyst was used for the oxidation of cyclohexene, DBT and diphenylsulfide. In each case the reaction products were easily separated from the appropriate catalyst by phase separation according to the principles described herein. It should be noted, that no evidence was found for catalyst leaching in these experiments.

The hydroformylation of olefins is an important industrial process for the production of aldehydes from olefins, carbon monoxide, and hydrogen in the presence of homogeneous cobalt or rhodium catalysts. One of the most challenging problems associated with commercial processes is the separation of high molecular weight aldehydes from the catalysts. The use of an aqueous (i.e., non-fluorous) biphase system, in which the water phase contains the dissolved transition metal catalysts, offers the easy separation of the organic products. However, since the catalytic reaction occurs in the aqueous phase, the potential application of the aqueous biphase system is limited by the solubility of the olefin in the water phase. In contrast, it is expected that fluorous multiphase systems may be used for a variety of olefins, as the solubility of higher olefins in fluorcarbons is much higher than in water and the aldehydes have limited miscibility with the fluorocarbons. The fluorous ligands P[$OCH_2CH_2(CF_2)_7CF_3$]$_3$ and P[$CH_2CH_2(CF_2)_5CF_3$]$_3$ were prepared in high yield. Both were isolated by distillation and characterized by NMR.

The hydroformylation reactions were performed under FMS conditions as disclosed herein and the results using the P[$CH_2CH_2(CF_2)_5CF_3$]$_3$ modified rhodium fluorous catalyst system showed after 11 hours the formation of 84.5% undecanals with normal/iso ratio of 2.9, 7.3% isomerization to internal decenes. After the reactions were complete, the reactor was cooled to room temperature and depressurized. The two phase systems were separated under $N_2$. The upper phases were recharged to the autoclave and showed no catalytic activity. These results indicate that the FMS catalysts do not leach catalytically active rhodium species into the hydrocarbon phase under hydroformylation conditions. By contrast when the lower phases were separated and recharged to the autoclave and additional olefin was added and the reaction proceeded as above. These results clearly establish the facile separation and reusability of fluorous catalysts. For comparison, the hydroformylation of decene-1 was also performed in toluene using the commercially used $PPh_3$, under similar conditions. After one hour the formation of 87.5% undecanals with normal/iso ratio of 2.8, and 12% isomerization to internal decenes was observed. Thus the benefits of easy separation and catalyst recycling of the present invention have been demonstrated.

When the similar reaction performed in the presence of the $P[OCH_2CH_2(CF_2)_7CF_3]_3$ modified rhodium fluorous catalyst system the formation of 32% undecanals with normal/iso ratio of 12.5, and isomerization to 7.5% internal decenes was observed after 10 hours.

The hydroformylation of decen-1 with $P[CH_2CH_2(CF_2)_5CF_3]_3$ modified cobalt fluorous catalyst system showed after 5 hours the formation of 37% undecanals with normal/iso ratio of 2.0, 36.5% undecanols with normal/iso ratio of 2.0, and 10% isomerization to internal decenes.

The inventions herein may suitably comprise, consist or consist essentially of the elements described herein.

EXAMPLES

Preparation of fluorous phase compatible catalysts

To demonstrate the preparation and solubility of FMS catalysts, the following was performed:

1. Preparation of Perfluorooctyl-phthalocyaninato iron(II)

A heavy wall pyrex tube containing a mixture of 0.1 mmol phthalocyaninato iron(II) and 1 mmol of perfluorooctyl iodide under argon was placed in a heatbath heated to 220° C. The temperature was increased from 220° C. to 300° C. in one hour then to 330° C. in two hours. After cooling the tube to room temperature, the crude reaction product was extracted using 100 ml perfluorohexane. The solvent was removed in vacuo at room temperature and all the volatile side products were removed in vacuo at 100° C.

2. Preparation of Perfluorooctyl-phthalocyaninato nickel(II)

A heavy wall pyrex tube containing a mixture of 0.1 mmol phthalocyaninato nickel(II) and 1 mmol of perfluorooctyl iodide under argon was heated in a heatbath at 270° C. for 12 hours. After cooling the tube to room temperature the crude reaction product was extracted using 50 mL perfluorhexane. The solvent was removed in vacuo at room temperature and all the volatile side products were removed by high vacuum at 1000° C. The product was extremely soluble in perfluoro(methylcyclohexane), perfluorohexane, and perfluoro-tributylamine. The test solution on standing for 6 months showed no visible evidence of catalyst leaching from the fluorous phase to the nonfluorous phase. This example demonstrates the change of metal center in the same fluorous ligand as compared to Example 1.

3. Preparation of Perfluorodecyl-phthalocyaninato cobalt(II)

A heavy wall pyrex tube containing a mixture of 0.5 mmol phthalocyaninato cobalt(II) and 5 mmol of perfluorodecyl iodide under argon was heated in a heatbath at 250° C. for 12 hours and the temperature was increased to 290° C. in 2 hours. After cooling the tube to room temperature, the crude reaction product was extracted using 40 mL perfluorhexane. The solvent was removed in vacuo at room temperature and all the volatile side products were removed by high vacuum at 100° C. The product was extremely soluble in perfluoro(methylcyclohexane), perfluorohexane, perfluorotributylamin. The test solution on standing for 6 months showed no visible evidence of catalyst leaching from the fluorous phase to the nonfluorous phase.

4. Preparation of Perfluoroalkyl-5,10,15,20-tetrakis(pentafluorophenyl)-21H,23H-porphine iron(III)chloride In a 23 mL heavy wall pressure tube under argon a mixture of 5,10,15,20-tetrakis(pentafluorophenyl)-21H, 23H-porphine iron(III)chloride (0.024 mmol, 0.025g) and the appropriate perfluoroalkyl iodide (5 mmol, 2.0 g of perfluorohexyl, 2.5 g of perfluorooctyl, and 2.9 g of perfluorodecyl, respectively) was heated in a metal bath at 205° C. for 4 days. The products were isolated by evaporating all the unreacted reagents and the volatile side products in vacuo (0.1 mmHg) at 100° C. The yields are quantitative. UV-VIS spectrum in $CF_2ClCCl_2F$ showed the Soret band at 440 nm for the perfluorohexylated product. All products are brown colored in the above solvent. These products are very soluble in perfluorohexane, perfluorotributylamine, etc. This example demonstrates the use of three different fluorous moieties on one metal center.

5. Preparation of Tris(1H,1H,2H,2H-perfluorodecyl)phosphite

A solution of 30 mmol 1H,1H,2H,2H-perfluorodecanol and 30 mmol absolute pyridine in 50 mL of abs. diethyl ether was cooled to 0°–5° C. under $N_2$. A solution of 10 mmol $PCl_3$ in 5 mL abs. diethyl ether was added in 5 minutes. The mixture was warmed up to room temperature and then refluxed for one hour. The white precipitate was filtered under $N_2$ and wash 3 times with 50 mL abs. diethyl ether. The solvent was removed in vacuo at 70° C. and the residue was distilled under 0.1Hg mm vacuum. The major fraction was collected between 180° and 185° C., 7.81 g 5.5 mmol (55%); MS:$M^+$=1420; $^{31}P$ NMR ($d_6$-$Et_2O$): 146.8 ppm.

6. Preparation of Tris(1H,1H,2H,2H-Perfluorodecyl)phosphine

To a stirred suspension of Mg turnings (1.21g 50 mmoles) in ether (50 mL) under $N_2$ was added a solution of 1H,1H, 2H,2H-perfluorodecyl iodide (33.7 g, 50 mmoles) over 30 minutes. The mixture was stirred and refluxed for 16 hours. A sample analyzed by GC after treating it with aqueous $NH_4Cl$ showed the presence of unreacted alkyliodide. Thus, more magnesium turnings (1 g, freshly activated with iodine) was added to the mixture and stirred and refluxed for 2 hours until all the alkyl iodide had reacted. The reaction mixture was filtered under $N_2$ and the clear ether solution of the Grignard reagent was titrated (18 mmoles were formed, corresponding to 36% yield). To this solution a solution of phosphorous trichloride (0.82 g; 6 mmoles) in ether (10 mL) was added under $N_2$ at 5° C. and stirred at room temperature overnight and then refluxed for two hours. The reaction mixture was treated with saturated aqueous $NH_4Cl$ solution (100 mL, $N_2$ purged) and the ether distilled off. The residue was extracted with $CO_2$ saturated $CF_2ClCCl_2F$ (6 times 100 ml). The extract was filtered and dried on $Na_2SO_4$. Upon evaporation 15 g crude product was obtained. This was fractionated at 0.20 mmHg pressure. The phosphine fraction collected at 170°–180° C. to give 2.23 g pale yellow solid (1.33 mmol; 22%) MS: $M^+$=672; $^{31}P$-NMR ($CF_2ClCCl_2F$): −25.3 ppm.

7. Preparation of Tris(1H,1H,2H,2H-perfluorooctyl)phosphine

A 100 mL glass lined autoclave was charged under $N_2$ with 35 g (100 mmol) 1H,1H,2H,2H-perfluoro-1-octene, 0.6 g azobisisobutyronitrile and charged with $PH_3$ (0.85 g, 25 mmol) at room temperature. The mixture was stirred and heated to 110° C. and kept at that temperature for 2 hours. After cooling the reactor to room temperature, the unreacted $PH_3$ was vented to a scrubber containing 37% formaline solution and 0.05% $RhCl_3$. GC and $^{31}P$-NMR analysis showed the formation of $H_2PR$ (2%), $HPR_2$ (4%), and $PR_3$ (20%) [$^{31}$P-NMR (CF$_2$ClCCl$_2$F): −139.3, −67.1 and −24.9 ppm, respectively]. Addition of more azobisisibutyronitrile (0.25 g) and heating at 80° C. for 8 hours resulted in the disappearance of the mono- and dialkyl-phosphine intermediates. The mixture was diluted with C$_6$F$_{14}$ (25 mL) and washed with toluene (4×15 mL). Distillation under vacuum (155° C./0.3 mmHg) yielded 26% tris(1H,1H,2H,2H-perfluorooctyl)phosphine.

8. Preparation of Tris(1H,1H,2H,2H-perfluorodecyl)phosphate

A solution of 52 mmol 1H,1H,2H,2H-perfluorodecanol and 52 mmol abs. pyridine in 50 mL of abs. diethylether was cooled to 0°–5° C. under N$_2$. A solution of 17.2 mmol OPCl$_3$ in 5 mL abs. diethyl ether was added in 10 minutes. The mixture was warmed up to room temperature and refluxed for four hours. The reaction mixture was diluted with 600 mL abs. diethyl ether and washed with water (4×50 mL). The white precipitate formed was filtered, dissolved in 300 mL CF$_2$ClCFCl$_2$ and washed with water (3 times 50 mL). The organic phase was mixed with Na$_2$SO$_4$ and the solvent was removed in vacuo at 25° C. The resulting 7.6 g white solid was 99% pure according GC (31%). $^{31}$P-NMR (CF$_2$ClCFCl$_2$): −1.62 ppm.

To demonstrate that FMS catalysts may be used to carry out known reactions, the following were performed.

9. Oxidation of Cyclohexene

A 10 mL glass pressure tube was charged with a fluorous biphase composition prepared from 1 mL cyclohexene (10 mmol) and a deep blue solution of 44 mg CoPC(C$_{10}$F$_{21}$)$_x$ (x is approx. 4: 0.02 mmol) in 2 mL C$_6$F$_{11}$CF$_3$. The tube was pressurized with 100 psi O$_2$ and shaken at 24° C. for 17 hours in a vertical position. The tube was depressurized and the light yellow upper phase was separated and analyzed by GC-MS to show the formation of 4% 2-cyclohexenone, 1% 2-cyclohexenol, 0.1% 2,3-epoxy-cyclohexanone, and trace amounts of cyclohexene epoxide.

10. Oxidation of Dibenzothiophene

A 10 mL glass pressure tube was charged with a fluorous biphase composition prepared from a colorless solution of 0.184 g (1 mmol) dibenzothiophene in 1 mL toluene and a greenish blue solution of 44 mg FePC(C$_8$F$_{17}$)$_x$ (x is approx. 6: 0.015 mmol) in 2 mL C$_6$F$_{11}$CF$_3$. The tube was pressurized with 100psi O$_2$ and shaken at 100° C. for 17 hours in a vertical position. The tube was depressurized and GC analysis of the colorless upper phase showed the formation of 1.4% dibenzothiophene sulfone.

11. Oxidation of Diphenyl sulphide

A 10 mL glass pressure tube was charged with a fluorous biphase composition prepared from a colorless solution of 0.186 g (1 mmol) diphenyl sulfide in 1 mL toluene and a greenish blue solution of 44 mg FePC(C$_8$F$_{17}$)$_x$ (x is approx. 6: 0.015 mmol) in 2 mL C$_6$F$_{11}$CF$_3$. The tube was pressurized with 100 psi O$_2$ and shaken at 100° C. for 17 hours in a vertical position. The tube was depressurized and GC analysis of the colorless upper phase showed the formation of 10% diphenyl sulfone.

12. Hydroformylation of Decene-1 with Rhodium Fluorous Catalysts

A fluorous catalyst composition of 2 mmol P[CH$_2$CH$_2$(CF$_2$)$_5$CF$_3$]$_3$ in 35 mL C$_6$F$_{11}$CF$_3$ and 12.9 mg (0.05 mmol) Rh(CO)$_2$(acetylacetonate) in 35 mL toluene was charged to a 300 mL autoclave under 75 psi CO/H$_2$(1:1) and heated to 100° C. A 75 mL pressure bomb was charged with 30 mL (160 mmol) decene-1 and attached to the autoclave. When the temperature in the autoclave reached 100° C., the decene-1 was added by using 150 psi CO/H$_2$(1:1) pressure which was maintained during the reaction. Samples were taken periodically and analyzed by GC. After 11 hours the reactor was cooled to room temperature. The autoclave was depressurized and the composition transferred into a separatory funnel under N$_2$. The upper phase was separated and shown by GC to contain 84.5% undecanals with normal/iso ratio of 2.9, and 7.3% internal decenes. The upper phase was recharged to the cleaned and catalytically inactive autoclave. A solution of 30 mL octene-1 in 35 mL toluene was added under 75 psi CO/H$_2$(1:1) and heated to 100° C. The pressure was increased to 150 psi CO/H$_2$(1:1) and maintained for 24 hours. GC analysis of the reaction mixture showed only trace amounts of conversion of octene-1. By contrast when the lower phase was also charged the hydroformylation of octene-1 proceeded to give 85% nonanals with normal/iso ratio of 2.9 and 8% internal octenes.

The hydroformylation of decene-1 was performed similarly with the P[OCH$_2$CH$_2$(CF$_2$)$_7$CF$_3$]$_3$ modified rhodium fluorous catalyst system. GC analysis of the upper phase after 10 hours showed the presence of 32% undecanals with normal/iso ratio of 12.5, and 7.5% internal decenes.

13. Hydroformylation of Decene-1 with Cobalt Fluorous Catalyst

A solution of 1 mmol P[CH$_2$CH$_2$(CF$_2$)$_5$CF$_3$]$_3$ in 17.5 mL C$_6$F$_{11}$CF$_3$ was mixed with 15 mL decene-1 (80 mmol) and charged to a 150 mL autoclave under N$_2$. The reactor was pressurized to 500 psi CO/H$_2$(1:1) and heated to 160° C. A 75 mL pressure bomb was charged with a solution of 0.05 mmol Co$_2$(CO)$_8$ in 17.5 mL toluene and attached to the autoclave. When the temperature in the autoclave reached 160° C., the toluene solution of Co$_2$(CO)$_8$ was added by using 1000 psi CO/H$_2$(1:1) forming the fluorous multiphase catalyst composition in situ under system conditions. The reaction pressure was maintained at 1000 psi using CO/H$_2$(1:1) during the reaction. Samples were taken periodically and analyzed by GC. After 5 hours the reactor was cooled to room temperature. The autoclave was depressurized and the composition transferred into a separatory funnel under N$_2$. The upper phase was separated and shown by GC to contain 37% undecanals with normal/iso ratio of 2.0, 36.5% undecanols with normal/iso ratio of 2.0, and 15% internal decenes.

14. Selective Extraction of n-Hexane from Perfluoromethylcyclohexane

When 2 g n-hexane and 5.7 g perfluoromethylcyclohexane was mixed at ambient conditions one liquid phase formed. Upon the addition of 1.7 g acetone to this solution phase separation occured, which were separated. While the upper phase contained 54 mol % n-hexane, 20 mol % perfluoromethylcyclohexane, and 26 mol % acetone, the lower phase contained 64 mol % n-hexane, 30 mol % perfluoromethylcyclohexane, and 6 mol % acetone. After two additional extraction of the lower fluorous phase with 0.87 g acetone the lower phase contained 6 mol % n-hexane, 90 mol % perfluoromethyl cyclohexane, and 4 mol % acetone. This example demonstrates that a one phase fluorous composition can be treated with a co-solvent to generate a two phase fluorous system.

14. Selective Extraction of Rhodium from Nonfluorous Phase

A solution of 2 mmol P[CH$_2$CH$_2$(CF$_2$)$_5$CF$_3$]$_3$ in 35 mL C$_6$F$_{11}$CF$_3$ was mixed with a light yellow solution of 12.9 mg (0.05 mmol) Rh(CO)$_2$-(acetylacetonate) in 35 mL toluene under argon at room temperature. The resulting fluorous biphase composition contained a colorless upper phase and a slightly yellow lower phase indicating the transfer of the rhodium from the toluene phase to the fluorous phase. The selective extraction of rhodium from the reddish solution of RhCl$_3$ in ethanol was performed similarly at 80° C., and resulted in a colorless upper phase and a light yellow lower phase. $^{31}$P-NMR of the lower phase revealed the formation of rhodium phosphine complexes.

What is claimed is:

1. A method of carrying out homogeneous catalytic chemical reactions, comprising:

forming a homogeneous liquid fluorous phase containing a fluorous solvent selected from the group consisting of fluorocarbons, fluorohydrocarbons, substituted fluorocarbons and substituted fluorohydrocarbons and mixtures thereof and a homogeneous catalyst functionalized to contain a sufficient number of fluorous moieties having the formula (R)$_n$(Rf)$_m$, wherein (R)$_n$ is a hydrocarbon domain and may be present or absent and n is an integer equal to at least zero and (Rf)$_m$ is at least one fluoroalkyl fluorous domain and m is a whole number, to render the functionalized catalyst preferentially soluble in the fluorous solvent; and contacting the functionalized catalyst with a nonfluorous phase containing a nonfluorous solvent having limited miscibility in the fluorous phase and having a Hildebrand solubility parameter of at least about 18.0 mPa½ and a reactant convertible in the presence of the functionalized catalyst to a product having low solubility in the fluorous solvent, wherein said contacting is carried out at conditions sufficient to produce said product.

2. The process of claim 1, further comprising separating the fluorous phase containing the functionalized catalyst and fluorous solvent from the nonfluorous phase containing the product and nonfluorous solvent.

3. The process of claim 1 wherein the catalyst is selected from the group consisting of homogeneous catalysts for unsaturates hydrogenation, olefin hydroformylation and alkane oxidation.

4. The process of claim 1 wherein n is an integer that renders (R)$_n$ effective to negate electron withdrawing effects of (Rf)$_m$.

5. The process of claim 1 wherein n is 0, 1 or 2.

6. The process of claim 1 wherein (R)$_n$ is hydrogen atom rich in comparison to (Rf)$_m$ and (Rf)$_m$ is fluorine atom rich in comparison to (R)$_n$.

7. A method for carrying out homogeneous stoichiometric chemical reactions, comprising:

forming a homogeneous liquid fluorous phase containing a fluorous solvent selected from the group consisting of fluorocarbons, fluorohydrocarbons, substituted fluorocarbons and substituted fluorohydrocarbons and mixtures thereof and a stoichiometric reagent functionalized to contain a sufficient number of fluorous moieties having the formula (R)$_n$(Rf)$_m$, wherein (R)$_n$ is a hydrocarbon domain and may be present or absent and n is an integer equal to at least zero and (Rf)$_m$ is at least one fluoroalkyl fluorous domain and m is a whole number, to render the functionalized stoichiometric reagent preferentially soluble in the fluorous solvent; and contacting the functionalized stoichiometric reagent with a nonfluorous phase containing a nonfluorous solvent having limited miscibility in the fluorous phase and having Hildebrand solubility parameter of at least about 18.0 MPa½ and containing a reactant convertible in the presence of the functionalized stoichiometric reagent to a product having low solubility in the fluorous solvent, wherein said contacting is carried out at reaction conditions sufficient to produce said product.

8. The process of claim 7, further comprising separating the fluorous phase containing the functionalized stoichiometric reagent and fluorous solvent from the nonfluorous phase containing the product and nonfluorous solvent.

9. The process of claim 7 wherein n is 0, 1 or 2.

10. The process of claim 7 wherein n is an integer that renders (R)$_n$ effective to negate electron withdrawing effects of (Rf)$_m$.

* * * * *